US008189188B2

(12) United States Patent
Busch et al.

(10) Patent No.: US 8,189,188 B2
(45) Date of Patent: *May 29, 2012

(54) METHODS FOR DETERMINING ENANTIOMERIC PURITY WITH VARYING CHIRAL ANALYTE CONCENTRATION

(75) Inventors: Kenneth W. Busch, Waco, TX (US); Jemina Rose Ingle, Lawrence, KS (US); Marianna Busch, Waco, TX (US)

(73) Assignee: Baylor University, Waco, TX (US)

( * ) Notice: Subject to any disclaimer, the term of this patent is extended or adjusted under 35 U.S.C. 154(b) by 498 days.

This patent is subject to a terminal disclaimer.

(21) Appl. No.: 12/083,163

(22) PCT Filed: Oct. 6, 2006

(86) PCT No.: PCT/US2006/039284
§ 371 (c)(1),
(2), (4) Date: Nov. 11, 2009

(87) PCT Pub. No.: WO2007/044602
PCT Pub. Date: Apr. 19, 2007

(65) Prior Publication Data
US 2010/0045969 A1    Feb. 25, 2010

Related U.S. Application Data

(60) Provisional application No. 60/724,861, filed on Oct. 7, 2005.

(51) Int. Cl.
*G01J 3/00* (2006.01)

(52) U.S. Cl. ....................................................... 356/300
(58) Field of Classification Search .................. 356/51, 356/301; 250/459.1; 324/309
See application file for complete search history.

(56) References Cited

OTHER PUBLICATIONS

U.S. Appl. No. 60/526,494; Busch, Kenneth W., et al., 2004.
U.S. Appl. No. 60/615,123, Busch, Kenneth W., 2004.
Otagiri, et al., Chem. Pharm. Bull., vol. 23, p. 188, 1975.
Cox, et al., J. Photochem. Photobiol., vol. 39, p. 597, 1984.
Park, et al., J. Phys. Chem., vol. 98 p. 6158, 1994.
Balabai, J. Phys. Chem., vol. 102, p. 9617, 1998.
Bortolus, et al., J. Phys. Chem. A, vol. 106, p. 1686, 2002.
Desiderio, et al., J. Chromatogr. A, vol. 807, pp. 37-56, 1998.
McCarroll, et al., J. Am. Chem. Soc., vol. 123, p. 317, 2001.
Pascoe, et al., Electrophoresis, vol. 21, pp. 2033-2042, 2000.
Schiller, et al., J. Chem. Soc., Faraday Trans., vol. 83, p. 3227, 1987.
Suzuki, Electronic Absorption Spectra and Geometry of Organic Molecules, p. 102, 1967.

*Primary Examiner* — Tarifur Chowdhury
*Assistant Examiner* — Abdullahi Nur
(74) *Attorney, Agent, or Firm* — Jackson Walker L.L.P.

(57) ABSTRACT

A new strategy for the quantitative determination of enantiomeric purity that combines guest-host complexation, spectroscopy, and chemometric modeling. Spectral data for samples of known enantiomeric composition is subjected to a type of multivariate regression modeling known as partial least squares ("PLS-1") regression. The PLS-1 regression produces a mathematical model that can be used to predict the enantiomeric composition of a set of samples of unknown enantiomeric purity. In this strategy, the concentration of the chiral compound does not have to be fixed or known.

37 Claims, 5 Drawing Sheets

METHODS FOR DETERMINING ENANTIOMERIC PURITY WITH VARYING CHIRAL ANALYTE CONCENTRATION

This application claims priority to U.S. Provisional Patent Application Ser. No. 60/724,861, entitled "METHODS FOR DETERMINING ENANTIOMERIC PURITY WITH VARYING CHIRAL ANALYTE CONCENTRATION" filed on Oct. 7, 2005, having K. Busch, J. Ingle and M. Busch, listed as the inventor(s), the entire content of which is hereby incorporated by reference.

BACKGROUND

This invention relates to a strategy for determining the enantiomeric purity of a compound through guest-host complexation, spectroscopy, and chemometric modeling. In particular, this invention relates to the determination of enantiomeric compositions of chiral compounds without regard to whether the concentration of the chiral compound remains constant.

Because of wide differences in the pharmacological and physiological properties of enantiomers, the determination of enantiomeric composition of chiral samples is of considerable interest to chemical research in general and the pharmaceutical industry in particular. In many cases, one enantiomer may be therapeutically active, while the other may be at best, non-active and at worst, toxic or lethal. The need for improved strategies for the assessment of enantiomeric purity arises from increased pressure on the pharmaceutical industry by government agencies for documentation on the pharmacological effects of individual enantiomers and the simultaneous demand in drug development for determination of enantiomeric excess in large combinatorial libraries. While many analytical techniques for chiral analysis have been developed over the years, gas and liquid chromatography, capillary electrophoresis and nuclear magnetic resonance are currently the most widely used. For high throughput screening strategies, slow chromatographic methods are not attractive. Rapid spectroscopic techniques are the most desirable.

Traditional methods of chiral analysis include chiroptical methods, in which the analyte interacts with incident polarized electromagnetic radiation. These include polarimetry, Raman optical activity, and electronic and vibrational circular dichroism. Non-chiroptical methods require some form of chiral auxiliary to interact with the enantiomers forming diastereomers. These include separation techniques, such as chromatography and capillary electrophoresis, NMR, and mass spectrometry.

Chromogenic enantioselective chiral hosts are capable of discriminating between enantiomers of chiral guests through a change in the visible absorption spectrum of the enantioselective complex, i.e., through a color change. (Otagiri, et al., *Chem. Pharm. Bull.*, vol. 23, p. 188, 1975; Schiller, et al., *J. Chem. Soc., Faraday Trans.*, vol. 83, p. 3227, 1987; Park, et al., *J. Phys. Chem.*, vol. 98, p. 6158, 1994; Cox, et al., *J. Photochem. Photobiol.*, vol.39, p. 597, 1984; Bortolus, et al., *J. Phys. Chem. A*, vol. 106, p. 1686, 2002; Balabai, *J. Phys. Chem.*, vol. 102, p. 9617, 1998). Under this strategy, the complexation of one enantiomer of a chiral substrate with a chiral host results in a visible spectral shift and/or the formation of an entirely new visible band, while little or no color change is observed when the other enantiomer complexes with the chiral host.

Traditonally, cyclodextrins are used as host molecules. Cyclodextrins ("CDs") are homochiral barrel-shaped sugar molecules that can form transient, non-covalent diastereomeric guest-host complexes with chiral guest molecules. Because the complexes that are formed are diastereomeric, they have different physical properties. Consequently, there are small changes in their spectra. (Suzuki, *Electronic Absorption Spectra and Geometry of Organic Molecules*, p. 102, 1967). These small spectral variations are often dismissed as having little utility for predicting the composition of a sample because the variations are small, the bands overlap, and the spectra do not appear to show a consistent trend (such as an offset) with composition. However, chemometric methods, such as multivariate regression, offer a variety of powerful techniques for revealing hidden relationships in data that are not immediately apparent.

Multivariate regression modeling ("MRM") is widely used in chemistry as a means of correlating spectral data with known compositional changes. (Martens, et al., *Multivariate Calibration*, 1989). While the use of chemometrics in near-infrared spectroscopy is well-established, its use in other spectral regions, such as the ultraviolet region, is not as common. MRM is used for the chemometric analysis of the spectral data of the solutions containing cyclodextrin guest-host inclusion complexes because the solution spectra are composite spectra, simultaneously containing contributions from complexed species (diastereomeric CD inclusion complexes) as well as uncomplexed species that are present because the complexation reaction is not complete.

U.S. Provisional Patent Application No. 60/526,494 pertains to the determination of the enantiomeric composition of various chiral guest molecules by multivariate regression modeling of spectral data obtained from solutions containing cyclodextrin as a chiral auxiliary. The premise behind the approach is that inclusion complex formation between the chiral guest analyte and the homochiral CD host results in the formation of transient diastereomeric inclusion complexes with different physical and spectral properties. As a result, it is observed that, for solutions containing a fixed chiral guest concentration and a fixed CD host concentration, the absorption or emission spectra vary slightly as the enantiomeric composition of the samples is changed. The small spectral variations are then correlated with the known enantiomeric composition of the guest analyte using standard multivariate regression modeling techniques such as partial-least-squares regression (PLS-1). U.S. Provisional Patent Application No. 60/615,123 pertains to a related method for determining enantiomeric purity, but it involves polarimetry as well.

One obvious limitation of the techniques described in U.S. Provisional Patent Applications Nos. 60/526,494 and 60/615,123 is the necessity of keeping the analyte concentration constant. This unrealistic constraint severely limits the usefulness of the technique, particularly in industry, where analyte concentration is likely to fluctuate around an average value.

SUMMARY

This invention relates to a new strategy for the quantitative determination of enantiomeric purity. The strategy combines guest-host complexation, spectroscopy, and chemometric modeling. In particular, a type of multivariate regression modeling known as partial least squares ("PLS-1") regression is used to develop a mathematical model that can be used to predict the enantiomeric composition of a set of samples. This strategy for determining enantiomeric purity is not dependent on maintaining a constant concentration of the chiral analyte.

Multivariate regression is widely known in many areas of chemistry and can serve as a particularly powerful computational tool for correlating spectral data with known compositional changes in a test set of samples. The basic objective of the method is to develop a mathematical model that relates two sets of variables to each other so that the independent or X-variables can be used to determine the dependent or Y-variable. In this case, the X-variables are the spectral information and the Y-variable is the enantiomeric composition.

To avoid problems with colinearity in the data, all multivariate regression techniques require an orthogonal basis set or coordinate system on which to represent the data. To achieve this condition, modern regression techniques employ projection methods to obtain a series of variance-scaled eigenvectors that can serve as a new coordinate system for the data. This form of data decomposition assures an orthogonal coordinate system for the data. At the same time, it provides a way to reduce the dimensionality of the data because only the major eigenvectors are needed to represent the data. Finally, when the data are represented on the new coordinate system, new insight is often gained as new relationships that were formerly obscured in the old coordinate system are revealed.

Compared with principal component regression, another well known method of MRM, the PLS-1 algorithm is especially powerful as a means of multivariate regression, because both the spectral data and the dependent variable (in this case, enantiomeric composition) are actively involved in the construction of the new basis set of variance-scaled eigenvectors that serve as PLS components. In this way, the PLS regression algorithm focuses on those aspects of the spectral data that are most important in predicting enantiomeric composition.

In previous methods for determining enantiomeric purity using guest-host complexation and chemometric modeling, a series of calibration standards, containing a fixed concentration of chiral analyte and a fixed concentration of chiral auxiliary (cyclodextrin) was prepared. The UV-visible absorption spectra of the calibration standards were then obtained and these spectra were then subjected to multivariate regression analysis with partial-least-squares (PLS-1) regression. The regression model was then used to predict the enantiometric purity of unknown samples from the absorption spectra of the unknowns. A major limitation in this procedure was the requirement of maintaining a fixed concentration of chiral analyte. In any real analytical situation, the concentration of the chiral analyte is not likely to be known or remain constant from sample to sample.

There are three general methods of determining enantiomeric purity while also dealing with varying analyte concentrations. The first is to make no special adjustment for the variance in concentration and rely on the statistical program to sort out the variances due to differences in enantiomeric composition in the presence of variances due to concentration differences. The second is to include the concentration as a variable, along with the spectral data, in the statistical model. The third is to normalize the spectra with respect to concentration (essentially dividing each absorbance value by the concentration) and then using the normalized spectra in the regression analysis. Although normalizing the spectra according to the third method gives the most accurate results, all methods are effective depending on the level of accuracy needed.

These methods allow for the successful determination of enantiomeric composition of an unknown sample even when both the concentration and the enantiomeric composition are unknown. Using regression analysis, spectral data can even be used to predict the concentration, the concentration can be used to normalize the data, and the normalized data can then be used to predict enantiomeric composition, with an average error of less than about 10%.

In the first general method, the spectral data are used as raw data without further modification in the regression model. In other words, the regression model is created without the inclusion of any information pertaining to concentration of the known samples. To create the regression model, principal component analysis is first used to select a spectral range in which the spectral differences that arise in each sample due to the influence of the enantiomeric composition of the guest molecule are most appreciable. PLS-1 regression of the spectral data for the selected wavelength range is performed for the data collected for each of the samples to determine the regression coefficients at each wavelength and to create the regression model that can predict the enantiomeric composition of the chiral analyte:

$$\hat{y}_{enantiopurity} = b_0 + b_1 A_1 + b_2 A_2 + \ldots + b_n A_n$$

where $\hat{y}_{enantiopurity}$ is the predicted enantiomeric composition of the chiral analyte, the b-values are the regression parameters from the model, and the A-values are the absorbances at the 1 to n wavelengths in the spectral data, and $b_0$ is the constant regression coefficient. Thus, the regression coefficient at each wavelength is multiplied by the absorbance of a sample measured at the same wavelength, to give a number represented as $b_i A_i$. This is done for each wavelength within the selected wavelength range. These numbers, along with the constant regression coefficient $b_0$, are then added together to give the enantiomeric composition of the unknown sample ($\hat{Y}_{enantiopurity}$). Spectral data is then collected for an unknown sample having an unknown concentration and an unknown enantiomeric composition. This spectral data is inserted into the regression model to predict the enantiomeric purity of the unknown sample.

To test the model, a sample of the unknown compound is prepared through guest-host complexation, utilizing the same host compound at the same concentration, but without regard to the concentration of the unknown chiral compound. Spectral data for the sample is collected at each wavelength in the selected range of wavelengths. The concentration of chiral analyte is then predicted using the model created. The spectral data is inserted into the regression vector above, allowing the calculation of the enantiomeric composition.

In the second general method, the spectral data are used to create a regression model in which concentration is included as a variable. The spectral data for the unknown sample is then inserted into this new regression vector to predict enantiomeric purity.

In the third general method, the spectral data are normalized with regard to concentration by dividing the spectral data by the known or predicted concentration of the sample. Although it is preferable to use the laboratory calculated concentration of the samples to normalize the data, this requirement is also a limitation because the concentration of the sample is not always known. Because the solutions obey Beer's Law, their concentrations can be calculated from the spectral data. Thus, another regression model can be created to predict the concentration of the chiral analyte in the samples rather than the enantiomeric composition:

$$\hat{y}_{concentration} = b_0 + b_1 A_1 + b_2 A_2 + \ldots + b_n A_n$$

where $\hat{y}_{concentration}$ is the predicted concentration of the chiral analyte, the b-values are the regression parameters from the model, and the A-values are the absorbances at the 1 to n wavelengths in the spectral data. The predicted concentrations can be used to normalize the spectral data.

In the next step of the third method, the normalized spectral data is used to create a regression model for predicting the enantiomeric composition of the chiral analyte:

$$\hat{y}_{enantiopurity} = b_0 + b_1 A_1 + b_2 A_2 + \ldots + b_n A_n$$

where $\hat{y}_{enantiopurity}$ is the predicted enantiomeric composition of the chiral analyte, the b-values are the regression parameters from the model, and the A-values are the normalized absorbances at the 1 to n wavelengths in the spectral data, and $b_0$ is the constant regression coefficient. Thus, the regression coefficient at each wavelength is multiplied by the normalized absorbance of an unknown sample measured at the same wavelength, to give a number represented as $b_i A_i$. This is done for each wavelength within the selected wavelength range. These numbers, along with the constant regression coefficient $b_0$, are then added together to give the enantiomeric composition of the unknown sample ($\hat{Y}_{enantiopurity}$).

Finally, to test the model, a sample of the unknown compound is prepared through guest-host complexation, utilizing the same host compound at the same concentration, but without regard to the concentration of the unknown chiral compound. Spectral data for the sample is collected at each wavelength in the selected range of wavelengths. The concentration of chiral analyte is then predicted using the model created, and the spectral data is divided by the predicted concentration to give the normalized spectral data. The normalized spectral data is inserted into the regression vector above, allowing the calculation of the enantiomeric composition.

In the current invention, chemometric analysis of spectral data of solutions containing cyclodextrin guest-host inclusion complexes is used to determine the enantiomeric purity of simple chiral compounds. The spectral data may be collected using any wavelength light. Useful spectroscopic techniques include near IR, IR, and far IR; near UV, UV, and far UV; Raman; and NMR. NMR is routinely used in chiral analysis with shift reagents. However, combined with chemometics some shift reagents whose "shift" is small may be found useful. The most preferable spectroscopic techniques include absorption UV spectrometry, fluorescence emission spectrometry, Raman spectrometry, and NMR.

The method is quite general and can apply to a diversity of compounds. Depending on the guest molecule, different hosts (alpha, beta, or gamma-CD, as well as synthetically modified cyclodextrins) may give somewhat better results in terms of correlation coefficients and prediction ability with future samples. The host compound can be any homochiral molecule capable of forming a diastereomeric compound or complex with the chiral guest compound. Potential chiral hosts include modified cyclodextrins, chiral crown ethers (coronands), chiral cryptands, chiral podands, and chiral calixarenes, as well as naturally occurring homochiral molecules like starch (beta-amylose). Any homochiral molecule that can form a diastereomeric compound or complex with the guest molecule is useful. Because the method depends solely on the changes produced in the spectrum of the complexed guest molecule as a result of differences in the binding conditions for the different enantiomeric forms of the guest molecule with the chiral host, it does not assume or depend on any particular stoichiometry of the guest/host complex. Whatever guest/host complexes may be present in the solution are not expected to vary because the concentrations of the guest and the host are fixed.

DETAILED DESCRIPTION OF PREFERRED EMBODIMENTS

The current invention pertains to methods for determining enantiomeric purity of solutions of compounds whose enantiomeric composition is unknown. The methods involve guest-host complexation, spectroscopy, and chemometric modeling. A type of multivariate regression modeling known as partial least squares ("PLS-1") regression is used to develop a mathematical model that can be used to predict the enantiomeric composition of a set of samples. The methods do not require that the concentration of the chiral compound be constant.

For solutions containing a fixed concentration of chiral analyte and a fixed concentration of host compound, the UV absorption spectra vary slightly as the enantiomeric composition of the chiral guest molecule is changed. These small spectral changes can then be correlated with the known enantiomeric composition of a training set of samples using standard multivariate regression modeling (partial-least-squares regression, "PLS-1").

In addition to UV absorption spectrometry, fluorescence spectrometry can also be used. Fluorescence spectrometry offers several potential instrumental advantages when compared with absorption spectrophotometry. For example, it is well established, from a purely instrumental standpoint, that fluorescence measurements are more sensitive than absorption measurements because it is easier to detect a small emission signal over a low background than it is to distinguish the difference between two large intensities (I and I°) as in absorbance. In addition, since fluorescence is an emission technique, it is somewhat easier to implement in certain situations, because it is not necessary to monitor both the incident and the transmitted intensity as required for absorption measurements. Other preferable spectroscopic techniques include Raman spectrometry and NMR.

While purely instrumental factors may influence the sensitivity of detection of an analyte, it should be realized that with chiral analysis by multivariate regression modeling of spectral data, the question of sensitivity is not based solely on instrumental considerations. The spectral information that is actually used in regression modeling is encoded in the shape of the band envelope (and the extent to which this shape varies with enantiomeric composition) and not with detecting the intensity of the band maximum over a small background (i.e., the conventional detection limit).

Figure 1:
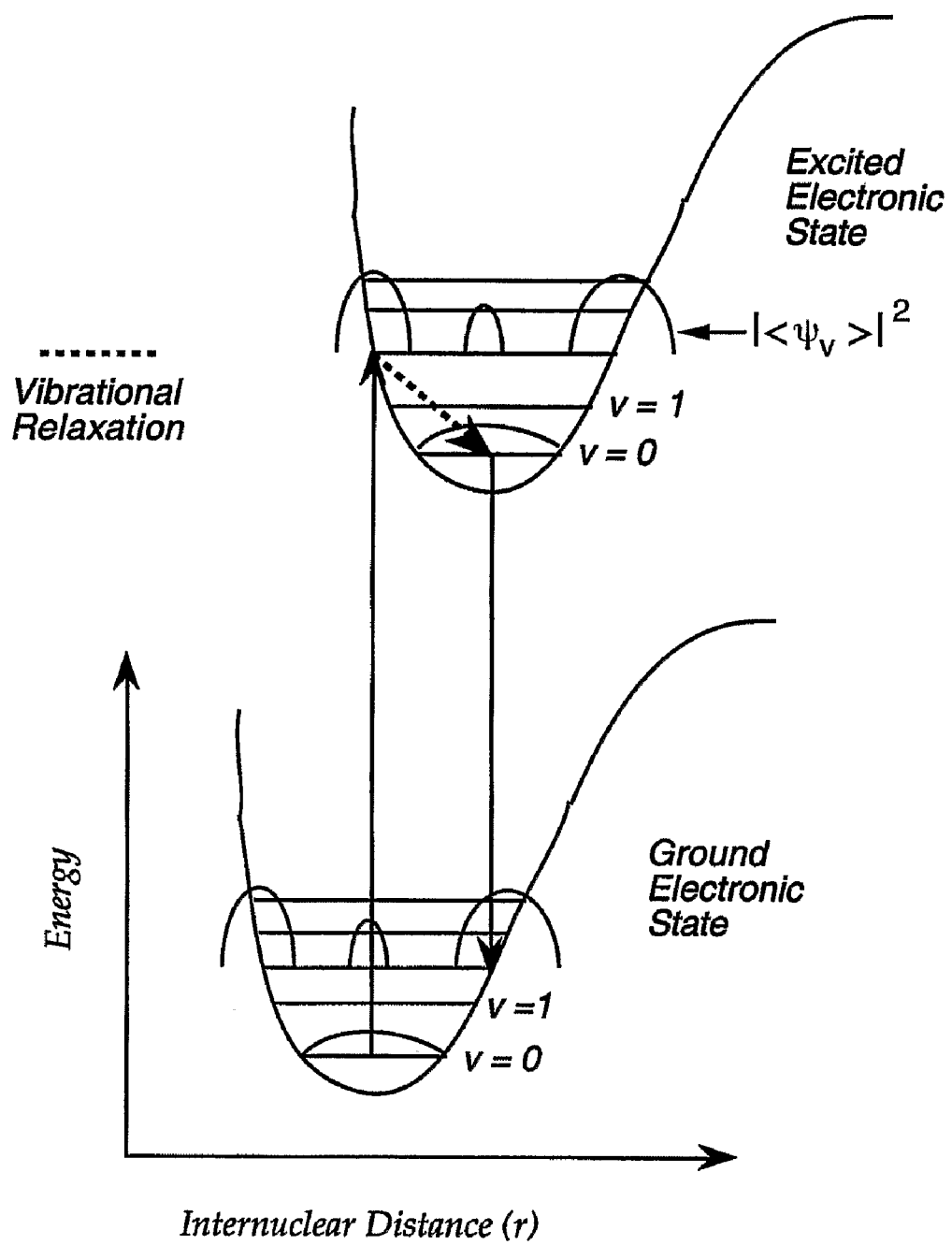
FIG. 1 shows the Morse potential representation of absorption and fluorescence transitions. $|\psi_v|^2$ is the square of the vibrational wavefunction for a given vibrational level.

While, at first glance, it might seem that fluorescence spectroscopy is simply another mode of observing electronic transitions, and is, therefore, little different from absorption measurements, there is a subtle fundamental difference between absorption and fluorescence measurements with respect to the band envelope that can potentially make the two modes of observation different, particularly with regard to the regression modeling of the band profile of the spectral data. This difference can be illustrated by the Morse-potential diagram shown in FIG. 1. As shown in FIG. 1, in absorption spectroscopy, an electronic transition occurs from the ground vibrational state of the ground electronic state to various excited vibrational levels of an excited electronic state. According to the Franck-Condon principle, an electronic transition will occur without changes in the positions of the nuclei (i.e., a vertical transition). In quantum mechanical terms, the probability of a transition is determined by $$|\langle \psi_{e''}\psi_{v''}|M|\psi_{e'}\psi_{v'}\rangle|^2 \quad (1)$$

where $\psi_e$ is the electronic wavefunction, $\psi_v$ is the vibrational wavefunction (the double prime indicates the ground state and the single prime indicates the excited state), and M is the transition moment operator. In accord with the Born-Oppenheimer approximation, Eqn. 1 can be written as the product of two terms $$|\langle \psi_{e''}|M|\psi_{e'}\rangle|^2 |\langle \psi_{v''}|\psi_{v'}\rangle|^2 \quad (2)$$

where the second term, known as the Franck-Condon factor, is the square of the overlap integral between the vibrational wavefunctions of the two states that are involved in the transition. Thus, in absorption, the strength of any given individual vibronic transition will be given by $$A \propto |\langle \psi_{v'}|\psi_{v''=0}\rangle|^2 \quad (3)$$

and the band profile of the absorption band will be governed by the strengths of these individual vibronic transitions as determined by their respective Franck-Condon factors.

In fluorescence, the situation is somewhat different. Here a molecule is excited by absorption of a photon from the ground vibrational level of the ground electronic state to various excited vibrational levels of the excited electronic state (exactly as it was in absorption) as shown in FIG. 1. However, before the molecule has time to fluoresce, it undergoes vibrational relaxation to the lowest vibrational level of the excited electronic state. Fluorescence then occurs from the lowest vibrational level of the excited electronic state to various excited vibrational levels in the ground electronic state. So, in fluorescence, the intensity of any given vibronic transition will be given by $$I_{fluor} \propto |\langle \psi_{v'=0}|\psi_{v''}\rangle|^2 \quad (4)$$

Once again, the band profile will be governed by the intensities of these individual vibronic transitions as determined by their respective Franck-Condon factors in Eqn. 4.

As shown in FIG. 1, a typical Morse potential for an anharmonic oscillator has a steep repulsive side (at short r, where r is the internuclear distance) and a less steep attractive side (at long r). In a $\pi \rightarrow \pi^*$ transition, it can be expected that the minimum of the upper state (which is $\pi^*$-like) will be shifted to longer r (less bound) as shown in FIG. 1, and absorption transitions will occur from v''=0 of the ground electronic state to the repulsive side of the upper state potential. As shown in FIG. 1, after vibrational relaxation, fluorescence transitions will occur to the attractive side of the ground-state potential well.

For situations like this, the Franck-Condon factors for absorption will be expected to be different from the Franck-Condon factors for fluorescence. Such differences should result in subtle differences in the shape of the band envelope that can be important in enantiomeric discrimination by regression analysis of spectral data. If the fluorescence process results in greater (or more uniform) spectral differences in the band envelope as a function of enantiomeric composition (i.e., greater enantiomeric discrimination), then fluorescence will be better than absorption when it comes to the regression modeling of the spectral data.

Naturally, in condensed-phase materials, the vibronic transitions that make up the band envelope will be broadened by solvent effects that arise from fluctuations in the structure of the solvation shell surrounding the chromophore. Such broadening is also likely to be affected by inclusion complex formation, which will affect both absorption and emission processes alike.

Multivariate modeling of the spectral data is a two-step procedure. In the first or calibration phase, a mathematical model in the form of a regression vector is determined with a training set of samples whose Y-variable is known. In particular, PLS-1 regression is used to construct a linear predictive model for enantiomeric compositions based on the spectral data. The equation below shows the typical format of a regression vector.

$$X_R = k_0 + k_1 A_1 + k_2 A_2 + \ldots + k_n A_n$$

In this equation, $X_R$ is the unknown mol fraction of guest molecule in the sample, $k_i$ are the coefficients of the regression vector, and $A_i$ are the absorbances at the different i wavelengths (i=1, . . . , n) for a given unknown sample. The variable $k_0$ is a constant regression coefficient. The regression coefficients ($k_i$) and the regression constant ($k_0$) are calculated using the PLS-1 regression algorithm, which may preferably be performed on a computer system utilizing suitable software (Unscrambler®, CAMO, Oslo, Norway).

The PLS-1 algorithm is especially powerful as a means of regression because both the X- and the Y-data are actively involved in the construction of the new basis set made up of PLS components. In this way, the PLS regression algorithm focuses on those aspects of the data that are most important in predicting Y. Partial least-squares regression has a goal of minimizing sample response prediction error by seeking linear functions of the predictors that explain as much variation in each response as possible, as well as accounting for variation in the predictors. The techniques implemented in the PLS-1 procedure work by extracting successive linear combinations of the predictors. In particular, the PLS-1 method balances the two objectives, seeking factors that explain both response and predictor variation.

In the second or validation phase of multivariate modeling, the mathematical model developed for the training set of samples is used to predict the enantiomeric composition of another independently obtained set of samples whose enantiomeric composition is also known. Here, the spectral data for the validation set of samples are obtained, and the equation above is used to predict the enantiomeric composition of the samples in the set from the measured spectral data. In this phase, the values of the Y-data predicted by the model are compared with the known values for the validation set.

Because of the impracticality of requiring that the concentration of the chiral compound be fixed and constant in a sample, it is preferable to let the concentration of the chiral analyte vary in the calibration standards. The spectral data can then be normalized by dividing them by the known concentrations of the chiral analyte before proceeding with the multivariate analysis. By dividing the spectral data by the concentration, the spectral data becomes independent of the concentration because the chiral analyte obeys Beer's Law:

$$A = abC$$

This equation relates the absorbance of the sample, A, to the absorptivity (a), the pathlength of the cell (b), and the concentration of the sample, C. When both sides of the equation are divided by C, this equation results:

$$(A/C) = ab$$

This equation shows that the right hand side is not independent of concentration. If the normalized spectral data are subjected to multivariate regression analysis after being divided by the known concentrations, the only source of spectral variation between samples is due to enantiomeric composition and experimental error.

There are three general methods for determining enantiomeric purity in instances where the concentration of the chiral analyte is not fixed or known. The procedure preferably involves the use of more than one set of calibration solutions using different concentration levels of the chiral analyte. Preferably, at least five sets of solutions should be used. Each set of calibration solutions preferably consists of a series of about ten solutions prepared using guest-host complexation, in which the guest molecule is the chiral compound whose enantiomeric composition is to be determined. The series of samples contains a known concentration of chiral analyte whose enantiomeric composition is varied between the solutions. A fixed amount of host compound is also added to each solution. Each series of samples uses a different concentration of chiral analyte.

All three general methods first require the collection of spectral data for for each sample of each series at various wavelengths using spectroscopy. The spectral data may be collected using any wavelength light. Useful spectroscopic techniques include near IR, IR, and far IR; near UV, UV, and far UV; Raman; and NMR. NMR is routinely used in chiral analysis with shift reagents. The most preferable spectroscopic techniques include absorption UV spectrometry, fluorescence emission spectrometry, Raman spectrometry, and NMR. The spectral data collected for all of the samples is then used in different manners to create regression models for the prediction of enantiomeric purity and, in some cases, concentration.

Broadly, a first aspect of the present invention involves a method for determining an unknown enantiomeric composition of a chiral compound in an unknown sample without using concentration of the chiral compound as a variable, comprising the steps of:

(1) Preparing a plurality of series of known samples, each of the known samples comprising a first complex, wherein, the first complex in each of the known samples comprises a ratio of a host compound and the chiral compound having a known enantiomeric composition, wherein in each of the known samples in any one series, the ratio of the chiral compound to the host compound remains the same and the enantiomeric composition of the chiral compound is varied, wherein in each of the known samples in any one series, the concentrations of the chiral compound and of the host compound are at a fixed or preset level, and wherein each series of known samples uses a different fixed concentration of chiral compound;

(2) Collecting spectral data of the known samples at various wavelengths;

(3) Performing a principal component analysis to select a spectral range of wavelengths in which the spectral differences arising in each of the known samples due to an influence of the enantiomeric composition is most appreciable to give the selected range of wavelengths;

(4) Performing a partial-least-squares regression of the spectral data over the selected range of wavelengths for each of the series of the known samples to determine a series of regression coefficients and a regression constant;

(5) Entering the series of regression coefficients for the selected range of wavelengths and the regression constant into a regression vector;

(6) Collecting spectral data of the unknown sample at various wavelengths to give unknown spectral data, wherein the unknown sample comprises a second complex having the same concentration of the host compound as that of the known samples, and wherein the concentration of the chiral compound in the unknown sample is unknown; and (7) Inserting the unknown spectral data into the regression vector to allow calculation of the unknown enantiomeric composition of the chiral compound in the unknown sample.

A second aspect of the present invention involves a method for determining an unknown enantiomeric composition of a chiral compound in an unknown sample with concentration of the chiral compound as a variable, comprising the steps of:

(1) Preparing a plurality of series of known samples, each of the known samples comprising a first complex, wherein, the first complex in each of the known samples comprises a ratio of a host compound and the chiral compound having a known enantiomeric composition, wherein in each of the known samples in any one series, the ratio of the chiral compound to the host compound remains the same and the enantiomeric composition of the chiral compound is varied, wherein in each of the known samples in any one series, the concentrations of the chiral compound and of the host compound are at a fixed or preset level, and wherein each series of known samples uses a different fixed concentration of chiral compound;

(2) Collecting spectral data of the known samples at various wavelengths;

(3) Performing a principal component analysis to select a spectral range of wavelengths in which the spectral differences arising in each of the known samples due to an influence of the enantiomeric composition is most appreciable to give the selected range of wavelengths;

(4) Performing a partial-least-squares regression of the spectral data over the selected range of wavelengths using concentration as a variable for each of the series of the known samples to determine a series of regression coefficients and a regression constant;

(5) Entering the series of regression coefficients for the selected range of wavelengths and the regression constant into a regression vector;

(6) Collecting spectral data of the unknown sample at various wavelengths to give unknown spectral data, wherein the unknown sample comprises a second complex having the same concentration of the host compound as that of the known samples, and wherein the concentration of the chiral compound in the unknown sample is unknown; and (7) Inserting the unknown spectral data into the regression vector to allow calculation of the unknown enantiomeric composition of the chiral compound in the unknown sample.

A further aspect of the present invention involves a method for determining an unknown enantiomeric composition of a chiral compound in an unknown sample with normalization of the spectral data using the known concentrations, comprising the steps of:

(1) Preparing a plurality of series of known samples, each of the known samples comprising a first complex, wherein, the first complex in each of the known samples comprises a ratio of a host compound and the chiral compound having a known enantiomeric composition, wherein in each of the known samples in any one series, the ratio of the chiral compound to the host compound remains the same and the enantiomeric composition of the chiral compound is varied, wherein in each of the known samples in any one series, the concentrations of the chiral compound and of the host compound are at a fixed or preset level, and wherein each series of known samples uses a different fixed concentration of chiral compound;

(2) Collecting spectral data of the known samples at various wavelengths;

(3) Normalizing the spectral data of the known samples by dividing the spectral data by the concentrations of the chiral compound in the known samples to give normalized spectral data;

(4) Performing a principal component analysis to select a spectral range of wavelengths in which the spectral differences arising in each of the known samples due to an influence of the enantiomeric composition is most appreciable to give the selected range of wavelengths;

(5) Performing a partial-least-squares regression of the normalized spectral data over the selected range of wavelengths for each of the series of the known samples to determine a series of regression coefficients and a regression constant;

(6) Entering the series of regression coefficients for the selected range of wavelengths and the regression constant into a regression vector;

(7) Collecting spectral data of the unknown sample at various wavelengths to give unknown spectral data, wherein the unknown sample comprises a second complex having the same concentration of the host compound as that of the known samples, and wherein the concentration of the chiral compound in the unknown sample is unknown; and (8) Inserting the unknown spectral data into the regression vector to allow calculation of the unknown enantiomeric composition of the chiral compound in the unknown sample.

An additional aspect of the present invention involves a method for determining an unknown enantiomeric composition of a chiral compound in an unknown sample with normalization of the spectral data using predicted concentrations, comprising the steps of:

(1) Preparing a plurality of series of known samples, each of the known samples comprising a first complex, wherein, the first complex in each of the known samples comprises a ratio of a host compound and the chiral compound having a known enantiomeric composition, wherein in each of the known samples in any one series, the ratio of the chiral compound to the host compound remains the same and the enantiomeric composition of the chiral compound is varied, wherein in each of the known samples in any one series, the concentrations of the chiral compound and of the host compound are at a fixed or preset level, and wherein each series of known samples uses a different fixed concentration of chiral compound;

(2) Collecting spectral data of the known samples at various wavelengths;

(3) Performing a principal component analysis to select a spectral range of wavelengths in which the spectral differences arising in each of the known samples due to an influence of the concentration is most appreciable to give the selected range of wavelengths;

(4) Performing a partial-least-squares regression of the spectral data over the selected range of wavelengths for each of the series of the known samples to determine a series of concentration regression coefficients and a concentration regression constant;

(5) Entering the series of concentration regression coefficients for the selected range of wavelengths and the concentration regression constant into a concentration regression vector for calculating predicted concentration of the chiral compound;

(6) Determining the predicted concentrations of the chiral compound in the known samples using the concentration regression vector and the spectral data;

(7) Normalizing the spectral data of the known samples by dividing the spectral data by the predicted concentrations of the chiral compound in the known samples to give normalized spectral data;

(8) Performing a principal component analysis to select a spectral range of wavelengths in which the spectral differences arising in each of the known samples due to an influence of the enantiomeric composition is most appreciable to give the selected range of wavelengths;

(9) Performing a partial-least-squares regression of the normalized spectral data over the selected range of wavelengths for each of the series of the known samples to determine a series of enantiopurity regression coefficients and an enantiopurity regression constant;

(10) Entering the series of enantiopurity regression coefficients for the selected range of wavelengths and the enantiopurity regression constant into an enantiopurity regression vector to predict enantiomeric concentration;

(11) Collecting spectral data of the unknown sample at various wavelengths to give unknown spectral data, wherein the unknown sample comprises a second complex having the same concentration of the host compound as that of the known samples, and wherein the concentration of the chiral compound in the unknown sample is unknown;

(12) Inserting the unknown spectral data into the concentration regression vector to allow calculation of the unknown concentration of the chiral compound in the unknown sample;

(13) Normalizing the unknown spectral data by dividing the unknown spectral data by the predicted concentration of the unknown sample to give normalized unknown spectral data; and

(14) Inserting the unknown normalized spectral data into the enantiopurity regression vector to allow calculation of the unknown enantiomeric composition of the chiral compound in the unknown sample.

These strategies are useful for determining the enantiomeric compositions of various chiral compounds, including amino acids and pharmaceuticals. Any chiral compound that forms a complex with a host molecule and has an absorption band in the selected spectral range can be used. Examples of potential chiral analytes or guest compounds include chiral alkanes, chiral alkenes, chiral aromatics, chiral amines, chiral alcohols, chiral carboxylic acids, chiral organo-halogens, chiral aldehydes, chiral ketones, chiral ethers, chiral aromatic amines, chiral aromatic alcohols, chiral aromatic acids, chiral heterocyclic compounds, chiral alkaloids, and compounds containing combinations of the above functionalities. In particular, the enantiomeric compositions of ibuprofen, norephedrine, phenylglycine ("φ-Gly"), tartaric acid, glycidyl butyrate, aspartic acid, phenylalanine, and arabinose can be determined. In the case of tartaric acid, the regression model has continued to correctly predict the enantiomeric composition of unknown samples for up to six months without the need for recalibration. Moreover, because the chiral analysis method does not depend on the specific rotation of the target molecule, it is especially valuable for compounds where polarimetric determinations are problematic due to small specific rotations.

Any homochiral compound known to be useful for complexation with chiral compounds may be used as a chiral selector or host compound in the guest/host complexation step. Preferably, the chiral selector possesses an inner hydrophobic cavity while being hydrophilic on the exterior. The chiral selector compound can be any of the native cyclodextrins, such as alpha, beta, and gamma cyclodextrin, modified cyclodextrins, such as methyl cyclodextrin, hydroxypropyl cyclodextrin, and carboxymethyl cyclodextrin, any of which can be in alpha, beta, and gamma form. In addition, the chiral selector compound can be a chiral crown ether, such as any tetra-substituted crown ether, like (+)-(18-Crown-6)-2,3,11,12-tetracarboxylic acid (Desiderio et al., 2000; Pascoe, et al., 2000). The chiral selector can also be a chiral surfactant such as those based on amino acids and dipeptides, like poly(sodium N-undecanoyl-L-leucylvalinate) (McCarroll, et al. 2001). Further examples of the chiral selector are any sugar, such as fructose, glucose, or sucrose, which are chiral and can be used to produce a chiral environment in solution. The chiral selector can also be any chiral carbohydrate and starch, such as beta-amylose, and any chiral solvent liquid available in single enantiomer form with desirable solvating properties, such as D- and L-limonene and R- and S-octanol. Other examples of the chiral selector include chiral dipeptides, such as L-leucyl-L-alanine hydrate. The chiral selector can also be any chiral cryptands, chiral podands, chiral calixarenes, and any naturally occurring homochiral molecules.

In preferred embodiments, cyclodextrin is used as the chiral selector. Cyclodextrins are ideal inclusion complexing agents for solubilizing lipophilic guest molecules in aqueous media because they have a central cavity providing a hydrocarbon-like environment while the exterior of the cavity is water-compatible due to the oxygens linking the glucose units.

Both small and large guest molecules can form complexes with chiral selector compounds because complexation is not limited to the formation of 1:1 complexes where the guest is small enough to fit in the cavity. For large guest molecules, a number of chiral selectors may act cooperatively through multiple interactions to form n:1 (host:guest) complexes.

EXAMPLE 1

Collection of Spectral Data for CD-Phenylalanine Complexes

The structure of phenylalanine is shown below.

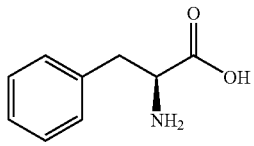

Phenylalanine is an essential amino acid and is also a component of the artificial sweetener aspartame.

Enantiomerically pure (D)-(+)-phenylalanine and (L)-(−)-phenylalanine and β-cyclodextrin hydrate were obtained from Aldrich Chemical Co. (Milwaukee, Wis.). A stock solution of 15 mM β-cyclodextrin was prepared in deionized water by weighing the solid reagent and diluting to volume in a volumetric flask. Stock solutions of phenylalanine were prepared at five concentration levels, centered around 7.5 mM and varying ±20 percent, as follows: 6.011 mM (X-Low), 6.744 mM (Low), 7.507 mM (Med), 8.233 mM (Hi), and 9.129 mM (X-Hi). Carefully weighed quantities of the analyte were dissolved in the stock CD solution. At each concentration level, solutions were then prepared that varied the enantiomeric composition; twenty solutions were prepared for X-Low, Low, Med and X-Hi and ten solutions were prepared at Hi, giving a total of 90 samples.

The spectra of the solutions were recorded with a Hewlett-Packard photodiode array (Model 8455) UV-Vis spectrometer using a 1.0 cm path length quartz cell over the wavelength range from 190-1100 nm.

Figure 2:
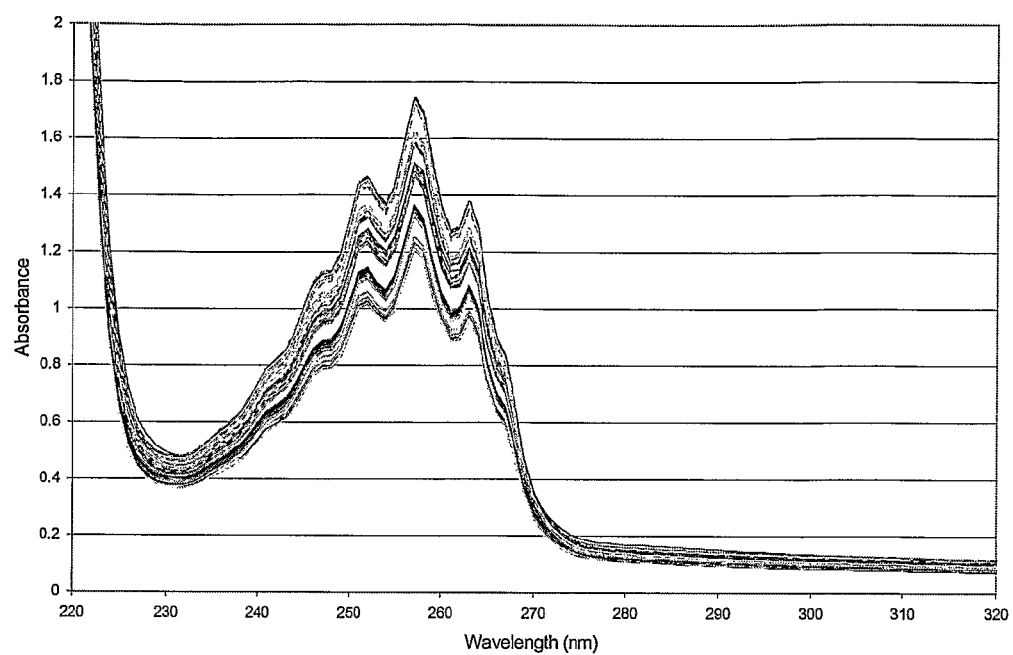
FIG. 2 shows the compiled raw UV/Visible spectra of 90 samples of phenylalanine+β-cyclodextrin in water.

FIG. 2 shows the UV absorption spectra obtained for the solutions containing a fixed β-cyclodextrin concentration (15 mM) and five concentration levels of phenylalanine with varying enantiomeric composition within each concentration level. The clear groupings of the five concentration levels and the spectral variations within each band are due to differences in enantiomeric composition.

Multivariate regression was performed with a commercial chemometric software package (Unscrambler™ vers. 7.6, CAMO, Inc., Corvallis, Oreg.). Principal component analysis and partial least-squares regression were performed on the data using full cross-validation. In the following examples, a random number generator was used to select 20 samples, some from every concentration level, to use as a test set. The regression models in each case were developed without these 20 samples. The models were used to predict the enantiomeric composition of the test set of samples, and these predicted values were compared with the known values to measure the predictability of the models.

EXAMPLE 2

Prediction of Enantiomeric Purity without use of Concentration as a Variable

Figure 3:
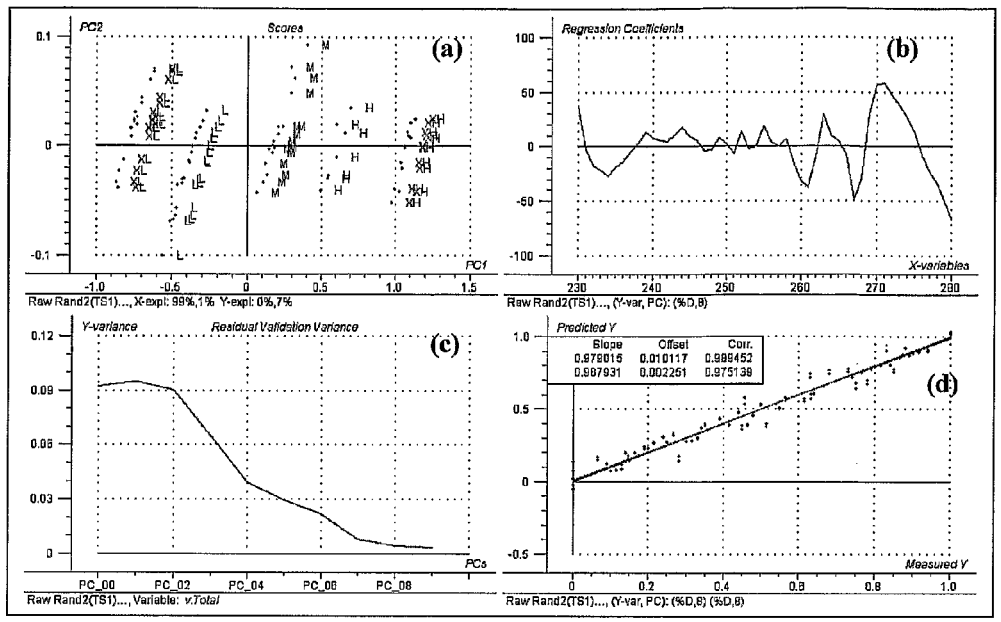
FIG. 3 shows a summary of the results for a PLS-1 regression of the spectral data as raw data with no concentration information included for guest-host complexes of phenylalanine+β-cyclodextrin in water over the wavelength range of 230-280 nm: (a) scores plot of the first principal component ("PC1") versus the second principal component ("PC2"); (b) regression coefficients as a function of wavelength; (c) residual variance as a function of the number of principal components; and (d) plot of the mole fraction of D-phenylalanine predicted by the model versus the known values.

In this phase, the raw spectral data from all concentration levels were used without further modification in the regression model. FIG. 3 shows a summary of the results of regression modeling. PLS regression modeling involves a transformation of the data set that plots the data on a new coordinate system. The axes of this new coordinate system are orthogonal, represent the areas of maximum variance of the data, and are known as PLS components. When the samples are plotted on the new coordinate system, the result is known as a scores plot. Scores plots are often useful because they can often reveal relationships among samples. FIG. 3(a) shows a two-dimensional PLS-scores plot of the first PLS component versus the second PLS component. The samples are identified by their concentration level. The samples are distributed by their concentration level along the horizontal axis. This would indicate that the first PLS component is concentration. Although the first two PLS components explain only 7% of the Y-variable (in this case enantiomeric composition), the third, fourth, and fifth components explain 29%, 35%, and 6%, respectively, while the remaining components contribute an additional 20%, bringing the total explained variance to 97%.

FIG. 3(b) is the plot of the regression coefficients versus wavelength. These coefficients make up the regression model that relates the predicted enantiomeric composition of a given sample to its measured absorption spectrum (i.e. the absorbances at wavelengths 1 to n). In this case, some wavelengths contribute positively to the model while others contribute negatively. FIG. 3(c) is a plot of the residual variance as a function of the number of PLS components. Here it can be seen that 8 PLS components are needed in the model. FIG. 3(d) is the plot of predicted enantiomeric composition of phenylalanine by the PLS-1 regression model versus the known laboratory-prepared enantiomeric compositions of the calibration samples. The correlation coefficient, the slope, and the offset are shown in the figure. A perfect model would have a correlation coefficient of 1, a slope of 1, and an offset of 0.

The test of any regression model is its ability to accurately predict the enantiomeric composition of future samples. To evaluate the performance and prediction capabilities of the model, the absorption spectra of the test set of 20 validation samples were recorded over the same wavelength range and the enantiomeric compositions were predicted from the spectral data using the regression model. It should be noted that the validation samples had different enantiomeric compositions from those used to prepare the model in the calibration phase. The prediction capability of the model is evaluated by calculating the root-mean-square of the absolute error and the percent relative error, per the following equation:

$$RMS\ Error = \sqrt{[(\Sigma(Error_i)^2)/n]}$$

where $Error_i$ is the error for the ith sample, and n is the number of samples in the test set. The results of the validation studies for the raw data analysis are shown in Table 1 below.

TABLE 1

| Actual φ D | Predicted φ D | Abs. Error | % RE |
|---|---|---|---|
| 0.490 | 0.511 | 0.021 | 4.29 |
| 0.590 | 0.591 | 0.001 | 0.169 |
| 0.690 | 0.660 | −0.030 | −4.35 |
| 0.715 | 0.689 | −0.026 | −3.64 |
| 1.000 | 1.036 | 0.036 | 3.60 |
| 0.050 | 0.023 | −0.027 | −54.4 |
| 0.600 | 0.583 | −0.017 | −2.83 |
| 0.650 | 0.617 | −0.033 | −5.08 |
| 0.700 | 0.663 | −0.037 | −5.29 |
| 0.221 | 0.277 | 0.056 | 25.3 |
| 0.293 | 0.325 | 0.032 | 10.9 |
| 0.705 | 0.561 | −0.144 | −20.4 |
| 0.080 | 0.128 | 0.048 | 60.0 |
| 0.230 | 0.154 | −0.076 | −33.0 |
| 0.380 | 0.362 | −0.018 | −4.74 |
| 0.430 | 0.513 | 0.038 | 19.3 |
| 0.530 | 0.556 | 0.026 | 4.91 |
| 0.580 | 0.535 | −0.045 | −7.76 |
| 0.930 | 1.005 | 0.075 | 8.07 |
| 1.000 | 0.980 | −0.020 | −2.00 |
| RMS Value | | 0.0528 | 21.8 |

EXAMPLE 3

Prediction of Enantiomeric Purity with Use of Concentration as a Variable

Figure 4:
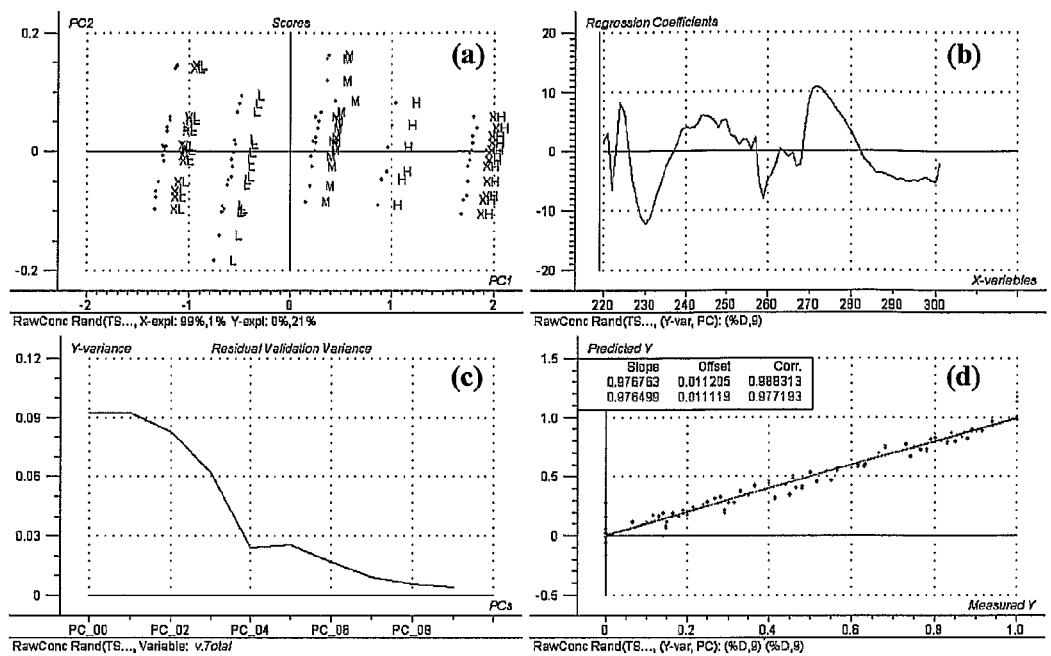
FIG. 4 shows a summary of the results for a PLS-1 regression of the spectral data with concentration included as a variable for guest-host complexes of phenylalanine+β-cyclodextrin in water over the wavelength range of 220-300 nm: (a) scores plot of the first principal component ("PC1") versus the second principal component ("PC2"); (b) regression coefficients as a function of wavelength; (c) residual variance as a function of the number of principal components; and (d) plot of the mole fraction of D-phenylalanine predicted by the model versus the known values.

In this phase, the concentration was included as a variable, along with the spectral data, in the regression model. FIG. 4 shows the regression results summary for this phase. Note again the distribution of the varying concentration levels along the horizontal axis in FIG. 4(a) (scores plot). In this case, the combined total of all of the PLS components explains 97% of the variance. In the validation phase, the same 20 samples were taken out to use as a test set, in order to make a consistent comparison. The results of the validation studies for the concentration as a variable analysis are shown in Table 2 below.

TABLE 2

| Actual φ D | Predicted φ D | Abs. Error | % RE |
|---|---|---|---|
| 0.490 | 0.528 | 0.038 | 7.76 |
| 0.590 | 0.552 | −0.038 | −6.44 |

TABLE 2-continued

| Actual φ D | Predicted φ D | Abs. Error | % RE |
|---|---|---|---|
| 0.690 | 0.732 | 0.042 | 6.09 |
| 0.715 | 0.680 | −0.035 | −4.90 |
| 1.000 | 0.983 | −0.017 | −1.70 |
| 0.050 | 0.079 | 0.029 | 57.1 |
| 0.600 | 0.579 | −0.021 | −3.50 |
| 0.650 | 0.595 | −0.055 | −8.46 |
| 0.700 | 0.674 | −0.026 | −3.71 |
| 0.221 | 0.216 | −0.005 | −2.26 |
| 0.293 | 0.280 | −0.013 | −4.44 |
| 0.705 | 0.637 | −0.068 | −9.65 |
| 0.080 | 0.112 | 0.032 | 40.0 |
| 0.230 | 0.206 | −0.024 | −10.4 |
| 0.380 | 0.393 | 0.013 | 3.42 |
| 0.430 | 0.461 | 0.031 | 7.20 |
| 0.530 | 0.513 | −0.017 | −3.21 |
| 0.580 | 0.481 | −0.099 | −17.1 |
| 0.930 | 0.928 | −0.002 | −0.215 |
| 1.000 | 0.930 | −0.070 | −7.00 |
| RMS Value | | 0.0410 | 17.0 |

EXAMPLE 4

Prediction of Enantiomeric Purity after Normalizing with known Concentration

Figure 5:
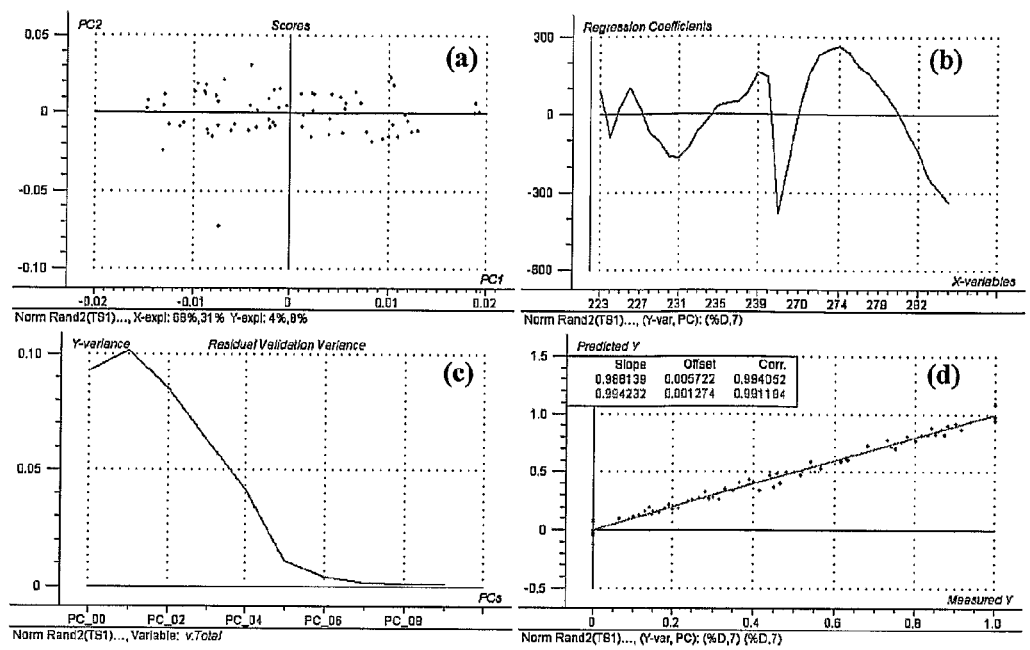
FIG. 5 shows a summary of the results for a PLS-1 regression of the spectral data with the data normalized with respect to known concentration for guest-host complexes of phenylalanine+β-cyclodextrin in water over the wavelength ranges of 223-240 nm and 268-85 nm: (a) scores plot of the first principal component ("PC1") versus the second principal component ("PC2"); (b) regression coefficients as a function of wavelength; (c) residual variance as a function of the number of principal components; and (d) plot of the mole fraction of D-phenylalanine predicted by the model versus the known values.

In this phase of the experiment, the spectra were normalized with respect to the laboratory-determined concentration. Each absorbance value was divided by the concentration of that sample, and then the normalized spectra were then used in the regression analysis. FIG. 5 shows a summary of the regression results for this analysis.

Firstly, in FIG. 5(a), it can be seen that the distribution of the scores plot by concentration level has been lost. The samples are now randomly scattered along the first two PLS components. In this case, fewer PLS components are needed to explain now 98% of the data. Also, the regression coefficients in FIG. 5(b) are smoother. (The sharp dip is due to the disconnect in the wavelength range used in the model.) The figures of merit in FIG. 5(d) are also better. The validation results for this analysis are shown in Table 3 below.

TABLE 3

| Actual φ D | Predicted φ D | Abs. Error | % RE |
|---|---|---|---|
| 0.490 | 0.524 | 0.034 | 6.94 |
| 0.590 | 0.587 | −0.003 | −0.508 |
| 0.690 | 0.749 | 0.059 | 8.55 |
| 0.715 | 0.695 | −0.020 | −2.80 |
| 1.000 | 0.964 | −0.036 | −3.60 |
| 0.050 | 0.039 | −0.011 | −22.2 |
| 0.600 | 0.588 | −0.012 | −2.00 |
| 0.650 | 0.598 | −0.052 | −8.00 |
| 0.700 | 0.665 | −0.035 | −5.00 |
| 0.221 | 0.230 | 0.009 | 4.07 |
| 0.293 | 0.276 | −0.017 | −5.80 |
| 0.705 | 0.647 | −0.058 | −8.23 |
| 0.080 | 0.080 | 0.000 | −0.175 |
| 0.230 | 0.232 | 0.002 | −0.870 |
| 0.380 | 0.421 | 0.041 | 10.8 |
| 0.430 | 0.461 | 0.031 | 7.21 |
| 0.530 | 0.564 | 0.034 | 6.42 |
| 0.580 | 0.588 | 0.008 | 1.38 |
| 0.930 | 0.928 | −0.002 | −0.215 |
| 1.000 | 1.042 | 0.042 | 4.20 |
| RMS Value | | 0.0316 | 7.34 |

EXAMPLE 5

Prediction of Enantiomeric Purity after Normalizing with Predicted Concentration Although normalization of the data results in the best predictive ability, even this step has a limitation, namely, that the concentration must be known in order to normalize the data. However, since these solutions obey Beer's Law, it should be possible to calculate the concentration from the spectra themselves. Although multivariate analysis is not strictly necessary for this case (a univariate calibration curve from the standard solutions should be sufficient), since multivariate regression is required in the second step, the same program was used to determine both concentration and enantiomeric composition. Multivariate regression predicted the concentration of the solutions with outstanding accuracy, as shown in Table 4 below.

TABLE 4

| Actual Conc (mM) | Predicted φ D | Abs. Error |
|---|---|---|
| 6.011 | 6.005 | −0.0998 |
| 6.011 | 6.020 | 0.150 |
| 6.011 | 6.010 | −0.0166 |
| 6.744 | 6.775 | 0.460 |
| 6.744 | 6.840 | 1.42 |
| 7.507 | 7.478 | −0.386 |
| 7.507 | 7.535 | 0.373 |
| 7.507 | 7.544 | 0.493 |
| 7.507 | 7.566 | 0.786 |
| 8.233 | 8.213 | −0.243 |
| 8.233 | 8.195 | −0.462 |
| 8.233 | 8.268 | 0.425 |
| 9.129 | 9.059 | −0.767 |
| 9.129 | 9.094 | −0.383 |
| 9.129 | 9.089 | −0.438 |
| 9.129 | 9.109 | −0.219 |
| 9.129 | 9.099 | −0.329 |
| 9.129 | 9.094 | −0.383 |
| 9.129 | 9.137 | 0.0876 |
| 9.129 | 9.113 | −0.175 |
| RMS % RE | | 0.507 |

These predicted concentrations were then used, instead of the laboratory-determined values, to normalize the spectra. These new normalized spectra were then used in the validation step, using the same regression model as before (FIG. 5). The validation results for this analysis are shown in Table 5 below.

TABLE 5

| Actual φ D | Predicted φ D | Abs. Error | % RE |
|---|---|---|---|
| 0.490 | 0.499 | 0.009 | 1.84 |
| 0.590 | 0.577 | −0.013 | −2.20 |
| 0.690 | 0.758 | 0.068 | 9.85 |
| 0.715 | 0.708 | −0.007 | −0.979 |
| 1.000 | 0.978 | −0.022 | −2.20 |
| 0.050 | 0.0349 | −0.015 | −30.2 |
| 0.600 | 0.588 | −0.012 | −2.00 |
| 0.650 | 0.605 | −0.045 | −6.92 |
| 0.700 | 0.702 | 0.002 | 0.286 |
| 0.221 | 0.196 | −0.025 | −11.3 |
| 0.293 | 0.245 | −0.048 | −16.4 |
| 0.705 | 0.584 | −0.121 | −17.2 |
| 0.080 | 0.0821 | 0.002 | 2.68 |
| 0.230 | 0.212 | −0.018 | −7.83 |
| 0.380 | 0.378 | −0.002 | −0.526 |
| 0.430 | 0.456 | 0.026 | 6.05 |
| 0.530 | 0.549 | 0.019 | 3.58 |
| 0.580 | 0.544 | −0.036 | −6.21 |
| 0.930 | 0.902 | −0.028 | −3.01 |
| 1.000 | 0.940 | −0.060 | −6.00 |
| RMS Value | | 0.0403 | 9.92 |

REFERENCES CITED

The following documents are hereby incorporated by reference.

U.S. PATENT DOCUMENTS

U.S. Provisional Patent Application Ser. No. 60/526,494
U.S. Provisional Patent Application Ser. No. 60/615,123

OTHER PUBLICATIONS

Balabai, *J. Phys. Chem.*, vol. 102, p. 9617, 1998
Bortolus, et al., *J. Phys. Chem. A*, vol. 106, p. 1686, 2002
Cox, et al., *J. Photochem. Photobiol.*, vol. 39, p. 597, 1984
Desiderio, et al., *J. Chromatogr. A*, vol. 807, pp. 37-56, 1998
McCarroll, et al., *J. Am. Chem. Soc.*, vol. 123, p. 317, 2001.
Otagiri, et al., *Chem. Pharm. Bull.*, vol. 23, p. 188, 1975
Park, et al., *J. Phys. Chem.*, vol. 98, p. 6158, 1994
Pascoe, et al., *Electrophoresis*, vol 21, pp. 2033-42, 2000
Schiller, et al., *J. Chem. Soc., Faraday Trans.*, vol. 83, p. 3227, 1987
Suzuki, *Electronic Absorption Spectra and Geometry of Organic Molecules*, p. 102, 1967

What is claimed is:

1. A method for determining an unknown enantiomeric composition of a chiral compound in an unknown sample without using concentration of the chiral compound as a variable, comprising:

preparing a plurality of series of known samples, each of the known samples comprising a first complex, wherein, the first complex in each of the known samples comprises a ratio of a host compound and the chiral compound having a known enantiomeric composition, wherein, in each of the known samples in any one series, the ratio of the chiral compound to the host compound remains the same and the enantiomeric composition of the chiral compound is varied, wherein, in each of the known samples in any one series, the concentrations of the chiral compound and of the host compound are at a preset level, and wherein each of the plurality of series of known samples has a different concentration of the chiral compound;

collecting spectral data of the known samples at various wavelengths;

performing a principal component analysis to select a spectral range of wavelengths in which the spectral differences arising in each of the known samples due to an influence of the enantiomeric composition is most appreciable to give the selected range of wavelengths;

performing a partial-least-squares regression of the spectral data over the selected range of wavelengths for each of the series of the known samples to determine a series of regression coefficients and a regression constant;

entering the series of regression coefficients for the selected range of wavelengths and the regression constant into a regression vector;

collecting spectral data of the unknown sample at the selected range of wavelengths to give unknown spectral data, wherein the unknown sample comprises a second complex having the same concentration of the host compound as that of the known samples, and wherein, in the unknown sample, the concentration of the chiral compound is unknown; and inserting the unknown spectral data into the regression vector to allow calculation of the unknown enantiomeric composition of the chiral compound in the unknown sample.

2. The method of claim 1, wherein the regression vector is:

$$X_R = k_0 + k_1 A_1 + k_2 A_2 + \ldots + k_n A_n,$$

and wherein:

$X_R$ is the unknown enantiomeric composition of the chiral compound in the unknown sample, $k_i$ is the series of regression coefficients calculated for each of the wavelengths in the selected range of wavelengths, $A_i$ is the spectral data of the unknown compound at each of the wavelengths in the selected range of wavelengths, i is the selected range of wavelengths, 1-n, and $k_0$ is the regression constant.

3. The method of claim 1, wherein the host compound comprises a homochiral molecule capable of forming a diastereomeric compound or complex with the chiral compound.

4. The method of claim 1, wherein the host compound is selected from the group consisting of modified cyclodextrins, chiral crown ethers, chiral surfactants, sugars, chiral carbohydrates, chiral solvents, chiral dipeptides, chiral cryptands, chiral podands, chiral calixarenes, and naturally occurring homochiral molecules.

5. The method of claim 1, wherein the host compound is selected from the group consisting of α-cyclodextrin, β-cyclodextrin, and γ-cyclodextrin.

6. The method of claim 1, wherein the chiral compound comprises a compound capable of forming a complex with the host compound and having an absorption band in the selected range of wavelengths.

7. The method of claim 1, wherein the chiral compound is selected from the group consisting of chiral alkanes, chiral alkenes, chiral aromatics, chiral amines, chiral alcohols, chiral carboxylic acids, chiral organo-halogens, chiral aldehydes, chiral ketones, chiral ethers, chiral aromatic amines, chiral aromatic alcohols, chiral aromatic acids, chiral heterocyclic compounds, chiral alkaloids, and compounds comprising combinations thereof.

8. The method of claim 1, wherein the chiral compound is selected from the group consisting of ibuprofen, norephedrine, phenylglycine, tartaric acid, glycidyl butyrate, aspartic acid, phenylalanine, and arabinose.

9. The method of claim 1, wherein the spectral data is UV absorption spectral data, fluorescence emission spectral data, Raman spectral data, or NMR spectral data.

10. A method for determining an unknown enantiomeric composition of a chiral compound in an unknown sample with concentration of the chiral compound as a variable, comprising:

preparing a plurality of series of known samples, each of the known samples comprising a first complex, wherein, the first complex in each of the known samples comprises a ratio of a host compound and the chiral compound having a known enantiomeric composition, wherein, in each of the known samples in any one series, the ratio of the chiral compound to the host compound remains the same and the enantiomeric composition of the chiral compound is varied, wherein, in each of the known samples in any one series, the concentrations of the chiral compound and of the host compound are at a preset level, and wherein each of the plurality of series of known samples has a different concentration of the chiral compound;

collecting spectral data of the known samples at various wavelengths;

performing a principal component analysis to select a spectral range of wavelengths in which the spectral differences arising in each of the known samples due to an influence of the enantiomeric composition is most appreciable to give the selected range of wavelengths;

performing a partial-least-squares regression of the spectral data over the selected range of wavelengths using concentration as a variable for each of the series of the known samples to determine a series of regression coefficients and a regression constant;

entering the series of regression coefficients for the selected range of wavelengths and the regression constant into a regression vector;

collecting spectral data of the unknown sample at the selected range of wavelengths to give unknown spectral data, wherein the unknown sample comprises a second complex having the same concentration of the host compound as that of the known samples, and wherein, in the unknown sample, the concentration of the chiral compound is unknown; and inserting the unknown spectral data into the regression vector to allow calculation of the unknown enantiomeric composition of the chiral compound in the unknown sample.

11. The method of claim 10, wherein the regression vector is:

$$X_R = k_0 + k_1 A_1 + k_2 A_2 + \ldots + k_n A_n,$$

and wherein:

$X_R$ is the unknown enantiomeric composition of the chiral compound in the unknown sample, $k_i$ is the series of regression coefficients calculated for each of the wavelengths in the selected range of wavelengths, $A_i$ is the spectral data of the unknown compound at each of the wavelengths in the selected range of wavelengths, i is the selected range of wavelengths, 1-n, and $k_0$ is the regression constant.

12. The method of claim 10, wherein the host compound comprises a homochiral molecule capable of forming a diastereomeric compound or complex with the chiral compound.

13. The method of claim 10, wherein the host compound is selected from the group consisting of modified cyclodextrins, chiral crown ethers, chiral surfactants, sugars, chiral carbohydrates, chiral solvents, chiral dipeptides, chiral cryptands, chiral podands, chiral calixarenes, and naturally occurring homochiral molecules.

14. The method of claim 10, wherein the host compound is selected from the group consisting of α-cyclodextrin, β-cyclodextrin, and γ-cyclodextrin.

15. The method of claim 10, wherein the chiral compound comprises a compound capable of forming a complex with the host compound and having an absorption band in the selected range of wavelengths.

16. The method of claim 10, wherein the chiral compound is selected from the group consisting of chiral alkanes, chiral alkenes, chiral aromatics, chiral amines, chiral alcohols, chiral carboxylic acids, chiral organo-halogens, chiral aldehydes, chiral ketones, chiral ethers, chiral aromatic amines, chiral aromatic alcohols, chiral aromatic acids, chiral heterocyclic compounds, chiral alkaloids, and compounds comprising combinations thereof.

17. The method of claim 10, wherein the chiral compound is selected from the group consisting of ibuprofen, norephedrine, phenylglycine, tartaric acid, glycidyl butyrate, aspartic acid, phenylalanine, and arabinose.

18. The method of claim 10, wherein the spectral data is UV absorption spectral data, fluorescence emission spectral data, Raman spectral data, or NMR spectral data.

19. A method for determining an unknown enantiomeric composition of a chiral compound in an unknown sample with normalization of the spectral data using known concentrations, comprising:
preparing a plurality of series of known samples, each of the known samples comprising a first complex, wherein, the first complex in each of the known samples comprises a ratio of a host compound and the chiral compound having a known enantiomeric composition,
wherein, in each of the known samples in any one series, the ratio of the chiral compound to the host compound remains the same and the enantiomeric composition of the chiral compound is varied, wherein, in each of the known samples in any one series, the concentrations of the chiral compound and of the host compound are at a preset level, and wherein each of the plurality of series of known samples has a different concentration of the chiral compound;
collecting spectral data of the known samples at various wavelengths;
normalizing the spectral data of the known samples by dividing the spectral data by the concentrations of the chiral compound in the known samples to give normalized spectral data;
performing a principal component analysis to select a spectral range of wavelengths in which the spectral differences arising in each of the known samples due to an influence of the enantiomeric composition is most appreciable to give the selected range of wavelengths;
performing a partial-least-squares regression of the normalized spectral data over the selected range of wavelengths for each of the series of the known samples to determine a series of regression coefficients and a regression constant;
entering the series of regression coefficients for the selected range of wavelengths and the regression constant into a regression vector;
collecting spectral data of the unknown sample at the selected range of wavelengths to give unknown spectral data, wherein the unknown sample comprises a second complex having the same concentration of the host compound as that of the known samples, and wherein, in the unknown sample, the concentration of the chiral compound is unknown; and
inserting the unknown spectral data into the regression vector to allow calculation of the unknown enantiomeric composition of the chiral compound in the unknown sample.

20. The method of claim 19, wherein the regression vector is:

$$X_R = k_0 + k_1 A_1 + k_2 A_2 + \ldots + k_n A_n,$$

and wherein:
$X_R$ is the unknown enantiomeric composition of the chiral compound in the unknown sample,
$k_i$ is the series of regression coefficients calculated for each of the wavelengths in the selected range of wavelengths,
$A_i$ is the spectral data of the unknown compound at each of the wavelengths in the selected range of wavelengths,
i is the selected range of wavelengths, 1-n, and
$k_0$ is the regression constant.

21. The method of claim 19, wherein the host compound comprises a homochiral molecule capable of forming a diastereomeric compound or complex with the chiral compound.

22. The method of claim 19, wherein the host compound is selected from the group consisting of modified cyclodextrins, chiral crown ethers, chiral surfactants, sugars, chiral carbohydrates, chiral solvents, chiral dipeptides, chiral cryptands, chiral podands, chiral calixarenes, and naturally occurring homochiral molecules.

23. The method of claim 19, wherein the host compound is selected from the group consisting of α-cyclodextrin, β-cyclodextrin, and γ-cyclodextrin.

24. The method of claim 19, wherein the chiral compound comprises a compound capable of forming a complex with the host compound and having an absorption band in the selected range of wavelengths.

25. The method of claim 19, wherein the chiral compound is selected from the group consisting of chiral alkanes, chiral alkenes, chiral aromatics, chiral amines, chiral alcohols, chiral carboxylic acids, chiral organo-halogens, chiral aldehydes, chiral ketones, chiral ethers, chiral aromatic amines, chiral aromatic alcohols, chiral aromatic acids, chiral heterocyclic compounds, chiral alkaloids, and compounds comprising combinations thereof.

26. The method of claim 19, wherein the chiral compound is selected from the group consisting of ibuprofen, norephedrine, phenylglycine, tartaric acid, glycidyl butyrate, aspartic acid, phenylalanine, and arabinose.

27. The method of claim 19, wherein the spectral data is UV absorption spectral data, fluorescence emission spectral data, Raman spectral data, or NMR spectral data.

28. A method for determining an unknown enantiomeric composition of a chiral compound in an unknown sample with normalization of the spectral data using predicted concentrations, comprising:
preparing a plurality of series of known samples, each of the known samples comprising a first complex, wherein, the first complex in each of the known samples comprises a ratio of a host compound and the chiral compound having a known enantiomeric composition,
wherein, in each of the known samples in any one series, the ratio of the chiral compound to the host compound remains the same and the enantiomeric composition of the chiral compound is varied, wherein, in each of the known samples in any one series, the concentrations of the chiral compound and of the host compound are at a preset level, and wherein each of the plurality of series of known samples has a different concentration of the chiral compound;
collecting spectral data of the known samples at various wavelengths;
performing a principal component analysis to select a spectral range of wavelengths in which the spectral differences arising in each of the known samples due to an influence of the concentration is most appreciable to give the selected range of wavelengths;
performing a partial-least-squares regression of the spectral data over the selected range of wavelengths for each of the series of the known samples to determine a series of concentration regression coefficients and a concentration regression constant;
entering the series of concentration regression coefficients for the selected range of wavelengths and the concentration regression constant into a concentration regression vector for calculating predicted concentration of the chiral compound;

determining the predicted concentrations of the chiral compound in the known samples using the concentration regression vector and the spectral data;

normalizing the spectral data of the known samples by dividing the spectral data by the predicted concentrations of the chiral compound in the known samples to give normalized spectral data;

performing a principal component analysis to select a spectral range of wavelengths in which the spectral differences arising in each of the known samples due to an influence of the enantiomeric composition is most appreciable to give the selected range of wavelengths;

performing a partial-least-squares regression of the normalized spectral data over the selected range of wavelengths for each of the series of the known samples to determine a series of enantiopurity regression coefficients and an enantiopurity regression constant;

entering the series of concentration regression coefficients for the selected range of wavelengths and the enantiopurity regression constant into an enantiopurity regression vector for calculating enantiomeric composition;

collecting spectral data of the unknown sample at the selected range of wavelengths to give unknown spectral data, wherein the unknown sample comprises a second complex having the same concentration of the host compound as that of the known samples, and wherein, in the unknown sample, the concentration of the chiral compound is unknown;

inserting the unknown spectral data into the concentration regression vector to allow calculation of the predicted unknown concentration of the chiral compound in the unknown sample;

normalizing the unknown spectral data by dividing the unknown spectral data by the predicted unknown concentration of the chiral compound in the unknown sample to give normalized unknown spectral data; and inserting the normalized unknown spectral data into the enantiopurity regression vector to allow calculation of the unknown enantiomeric composition of the chiral compound in the unknown sample.

29. The method of claim 28, wherein the concentration regression vector is:

$$X_R = k_0 + k_1 A_1 + k_2 A_2 + \ldots + k_n A_n,$$

and wherein:

$X_R$ is the unknown concentration of the chiral compound in the unknown sample, $k_i$ is the series of concentration regression coefficients calculated for each of the wavelengths in the selected range of wavelengths, $A_i$ is the spectral data of the unknown compound at each of the wavelengths in the selected range of wavelengths, i is the selected range of wavelengths, 1-n, and $k_0$ is the concentration regression constant.

30. The method of claim 28, wherein the enantiopurity regression vector is:

$$X_R = k_0 + k_1 A_1 + k_2 A_2 + \ldots + k_n A_n,$$

and wherein:

$X_R$ is the unknown enantiomeric composition of the chiral compound in the unknown sample, $k_i$ is the series of enantiopurity regression coefficients calculated for each of the wavelengths in the selected range of wavelengths, $A_i$ is the normalized spectral data of the unknown compound at each of the wavelengths in the selected range of wavelengths, i is the selected range of wavelengths, 1-n, and $k_0$ is the enantiopurity regression constant.

31. The method of claim 28, wherein the host compound comprises a homochiral molecule capable of forming a diastereomeric compound or complex with the chiral compound.

32. The method of claim 28, wherein the host compound is selected from the group consisting of modified cyclodextrins, chiral crown ethers, chiral surfactants, sugars, chiral carbohydrates, chiral solvents, chiral dipeptides, chiral cryptands, chiral podands, chiral calixarenes, and naturally occurring homochiral molecules.

33. The method of claim 28, wherein the host compound is selected from the group consisting of α-cyclodextrin, β-cyclodextrin, and γ-cyclodextrin.

34. The method of claim 28, wherein the chiral compound comprises a compound capable of forming a complex with the host compound and having an absorption band in the selected range of wavelengths 35. The method of claim 28, wherein the chiral compound is selected from the group consisting of chiral alkanes, chiral alkenes, chiral aromatics, chiral amines, chiral alcohols, chiral carboxylic acids, chiral organo-halogens, chiral aldehydes, chiral ketones, chiral ethers, chiral aromatic amines, chiral aromatic alcohols, chiral aromatic acids, chiral heterocyclic compounds, chiral alkaloids, and compounds comprising combinations thereof.

36. The method of claim 28, wherein the chiral compound is selected from the group consisting of ibuprofen, norephedrine, phenylglycine, tartaric acid, glycidyl butyrate, aspartic acid, phenylalanine, and arabinose.

37. The method of claim 28, wherein the spectral data is UV absorption spectral data, fluorescence emission spectral data, Raman spectral data, or NMR spectral data.

* * * * *